US006077055A

United States Patent [19]
Vilks

[11] Patent Number: 6,077,055
[45] Date of Patent: Jun. 20, 2000

[54] PUMP SYSTEM INCLUDING CASSETTE SENSOR AND OCCLUSION SENSOR

[75] Inventor: Clinton Scott Vilks, Plymouth, Minn.

[73] Assignee: SIMS Deltec, Inc., St. Paul, Minn.

[21] Appl. No.: 09/204,799

[22] Filed: Dec. 3, 1998

[51] Int. Cl.[7] .................................................. F04B 43/08
[52] U.S. Cl. ........................... 417/478; 417/44.2; 604/65; 604/67
[58] Field of Search ............................. 417/478, 63, 413, 417/44.2; 604/65, 151, 67, 153; 436/53

[56] References Cited

U.S. PATENT DOCUMENTS

| | | |
|---|---|---|
| 3,985,133 | 10/1976 | Jenkins et al. . |
| 4,191,184 | 3/1980 | Carlisle . |
| 4,210,138 | 7/1980 | Jess et al. . |
| 4,213,454 | 7/1980 | Shim . |
| 4,309,993 | 1/1982 | Brown . |
| 4,369,780 | 1/1983 | Sakai . |
| 4,373,525 | 2/1983 | Kobayashi . |
| 4,394,862 | 7/1983 | Shim . |
| 4,482,347 | 11/1984 | Borsanyi .................................. 604/153 |
| 4,526,574 | 7/1985 | Pekkarinen . |
| 4,559,038 | 12/1985 | Berg et al. . |
| 4,563,179 | 1/1986 | Sakai . |
| 4,565,542 | 1/1986 | Berg . |
| 4,617,014 | 10/1986 | Cannon et al. . |
| 4,650,469 | 3/1987 | Berg et al. . |
| 4,657,490 | 4/1987 | Abbott .................................... 417/478 |
| 4,671,792 | 6/1987 | Borsanyi . |
| 4,690,673 | 9/1987 | Bloomquist . |
| 4,710,163 | 12/1987 | Butterfield . |
| 4,790,816 | 12/1988 | Sundblom et al. . |
| 4,816,019 | 3/1989 | Kamen . |
| 4,836,752 | 6/1989 | Burkett . |
| 4,846,792 | 7/1989 | Bobo, Jr. et al. . |
| 4,850,807 | 7/1989 | Frantz ....................................... 417/63 |
| 4,852,581 | 8/1989 | Frank . |
| 4,856,339 | 8/1989 | Williams . |
| 4,878,896 | 11/1989 | Garrison et al. . |
| 4,882,575 | 11/1989 | Kawahara . |
| 4,927,411 | 5/1990 | Pastrone et al. . |
| 4,950,244 | 8/1990 | Fellingham et al. . |
| 4,976,151 | 12/1990 | Morishita . |
| 4,979,940 | 12/1990 | Bobo, Jr. et al. . |
| 5,006,050 | 4/1991 | Cooke et al. ............................ 417/478 |
| 5,062,774 | 11/1991 | Kramer et al. .......................... 417/413 |
| 5,096,385 | 3/1992 | Georgi et al. . |
| 5,103,211 | 4/1992 | Daoud et al. . |
| 5,108,367 | 4/1992 | Epstein et al. . |
| 5,154,700 | 10/1992 | Danby . |
| 5,181,910 | 1/1993 | Scanlon . |
| 5,190,522 | 3/1993 | Wojcicki et al. . |
| 5,213,573 | 5/1993 | Sorich et al. . |
| 5,217,355 | 6/1993 | Hyman et al. . |

(List continued on next page.)

FOREIGN PATENT DOCUMENTS

| | | |
|---|---|---|
| 0 328 162 B1 | 8/1989 | European Pat. Off. . |
| 0 371 507 B1 | 6/1990 | European Pat. Off. . |
| 0 468 603 A3 | 1/1992 | European Pat. Off. . |
| 0 551 088 A1 | 7/1993 | European Pat. Off. . |
| WO 87/07161 | 12/1987 | WIPO . |
| WO 91/16609 | 10/1991 | WIPO . |

OTHER PUBLICATIONS

"From Perception to Perfection: The Topflight Custom Membrane Switch", *Topflight Corporation, Membrane Switch Division*, A Designer's Guide brochure, 13 pages plus 3 cover sheets (Date Unknown).

"IV7000 Service Manual", Valleylab, Inc., pp. 27–34, including Table of Contents and Cover Sheet, (Copyright © 1988).

*Primary Examiner*—Teresa Walberg
*Assistant Examiner*—Leonid Fastovsky
*Attorney, Agent, or Firm*—Merchant & Gould P.C.

[57] ABSTRACT

A sensing device for a pump control module is described that is designed for use with a cassette having a pump surface with a projection. The sensing device is positioned on an interface surface of a pump control module, and includes an occlusion sensor and a cassette identification sensor. A pump control module, a cassette and a method of use are also described for administering a drug to a patient through a delivery conduit, utilizing the sensing device.

14 Claims, 11 Drawing Sheets

U.S. PATENT DOCUMENTS

| | | |
|---|---|---|
| 5,244,463 | 9/1993 | Cordner, Jr. et al. . |
| 5,356,378 | 10/1994 | Doan . |
| 5,364,242 | 11/1994 | Olsen . |
| 5,380,665 | 1/1995 | Cusack et al. .......................... 436/53 |
| 5,395,321 | 3/1995 | Kawahara et al. . |
| 5,431,627 | 7/1995 | Pastrone et al. . |
| 5,464,391 | 11/1995 | DeVale . |
| 5,464,392 | 11/1995 | Epstein et al. .......................... 604/67 |
| 5,531,697 | 7/1996 | Olsen et al. . |
| 5,531,698 | 7/1996 | Olsen . |
| 5,558,639 | 9/1996 | Gamgemi et al. ...................... 604/67 |
| 5,628,619 | 5/1997 | Wilson . |
| 5,647,854 | 7/1997 | Olsen et al. . |
| 5,683,367 | 11/1997 | Jordan et al. . |
| 5,695,473 | 12/1997 | Olsen . |
| 5,791,880 | 8/1998 | Wilson . |
| 5,807,075 | 9/1998 | Jacobsen et al. ...................... 417/44.2 |
| 5,935,099 | 8/1999 | Peterson et al. ....................... 604/65 |
| 5,989,222 | 11/1999 | Cole et al. ............................. 604/151 |

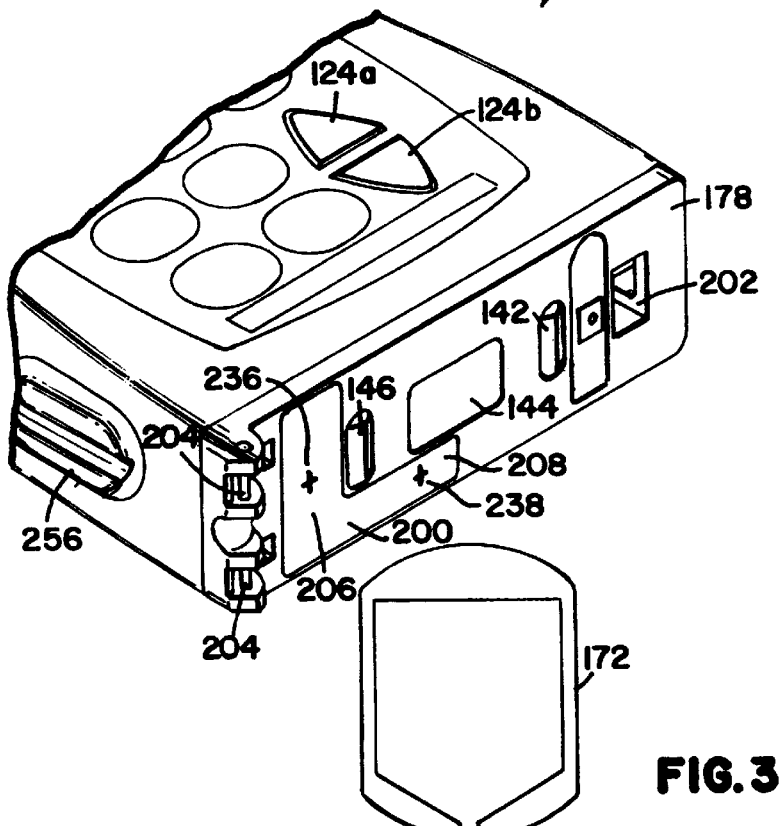
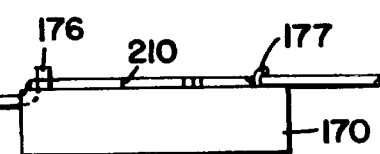
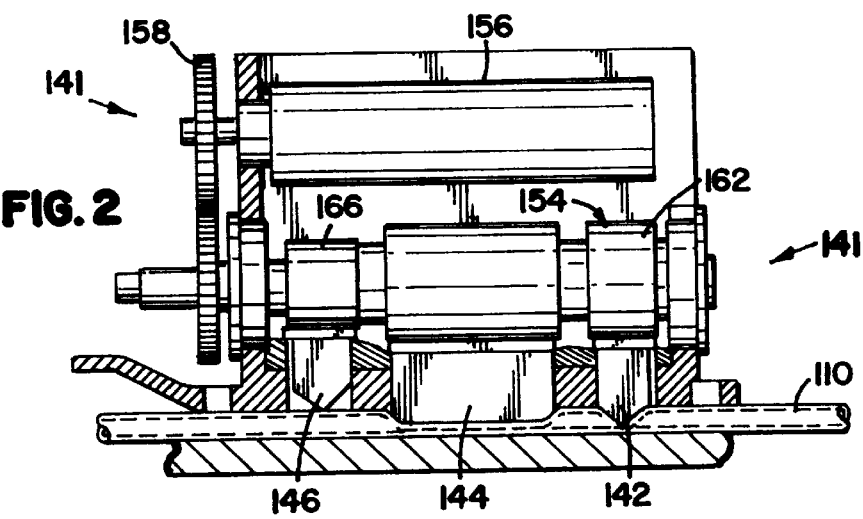

6,077,055

PUMP SYSTEM INCLUDING CASSETTE SENSOR AND OCCLUSION SENSOR

FIELD OF THE INVENTION

The present invention is directed to a pump system for use with a drug cassette for administering drugs, and more particularly to a system and method for administering drugs that employs a cassette identification sensor and an occlusion sensor.

BACKGROUND OF THE INVENTION

Various ambulatory medical devices are known for treating and/or monitoring patients at a remote site away from the caregiver's or clinician's office. One example of an ambulatory medical device is a drug delivery device, such as a drug pump, for providing periodic or continuous drug delivery to the patient when the patient is away from the caregiver's office. Ambulatory drug pumps are shown for example in U.S. Pat. Nos. 4,559,038, 5,531,697 and 5,695,473, the disclosures of which are incorporated by reference.

Certain drugs rarely achieve their maximum therapeutic action through conventional injection techniques. Many drugs reach their full potential only through precise delivery over an extended period of time. With controlled drug infusion through a drug pump, the drug can be given at a precise rate that will keep the drug concentration within the therapeutic margin and out of the toxic range. Ambulatory drug pumps can provide appropriate drug delivery to the patient at a controllable rate which does not require frequent medical attention and which allows the patient to leave the hospital or caregiver's office.

Ambulatory drug pumps and a patient's usage of ambulatory drug pumps should be monitored to ensure the maximum benefit to the patient and to ensure the patient's safety. For example, one concern is that delivery of the drug is not interrupted by a blockage in the tubing that delivers the drug to the patient. Blockage of this tubing by kinking or pinching, for example, may interfere with the accurate administration of the drug to the patient. Another concern is that the drug cassette may become disconnected from the drug pump, also interfering with the administration of the proper amount of drug to the patient.

Components used on an ambulatory drug pump may be used by the patient for extended periods of time and may be transported regularly subject to some bumping and jostling during use. One concern is that all components of the drug pump are reliable and durable. Another concern is that the occlusion pressure detection threshold is appropriate for the intended application of the drug pump, and that the drug pump functions appropriately for the intended application. Another concern is that drug pump components are preferably inexpensive to repair when necessary. Further concerns relate to the cost of manufacture and maintenance of the drug pump.

There is a need for a drug pump system which addresses these concerns and other concerns.

SUMMARY OF THE INVENTION

The present invention is a sensing device for a pump control module designed for use with a cassette having a pump surface with a projection and a method of use of the sensing device. The sensing device serves to sense the projection and sense occlusions in the tubing that delivers the drug to the patient. The sensing device is positioned on an interface surface of the pump control module. The sensing device supplies control signals for the pump control module indicative of the presence of the cassette projection and/or an occlusion in the delivery conduit.

The sensing device includes a first layer having a bottom surface with a first occlusion conductive pattern and a first identification conductive pattern. A second layer is also provided that has a top surface with a second occlusion conductive pattern aligned with the first occlusion conductive pattern of the first layer and a second identification conductive pattern aligned with the first identification conductive pattern of the first layer. In one embodiment, the sensing device includes a spacer layer positioned between the first layer and second layer, where the spacer layer defines an occlusion opening between the occlusion conductive patterns and an identification opening between the identification conductive patterns.

Another embodiment of the present invention is a pump control module for administering a drug to a patient through a delivery conduit, where the control module is designed for use with the cassette that has a projection. The control module of the present invention includes an interface surface and a membrane switch positioned on the interface surface. A membrane switch includes an occlusion sensor and an identification sensor. The identification sensor is configured to detect the projection on the cassette, while the occlusion sensor is configured to detect an occlusion, as may be evident by an overpressure condition, in the delivery conduit.

BRIEF DESCRIPTION OF THE DRAWINGS

FIG. 2 is a front view of the pump mechanism of the control module of the drug pump of FIG. 1.

FIG. 3 is an alternate cassette to the cassette shown in FIG. 1.

FIG. 4 is a bottom perspective view of the control module of FIG. 1.

DETAILED DESCRIPTION OF PREFERRED EMBODIMENTS

A sensing device for use with a drug pump is described herein. The sensing device includes a membrane switch having a cassette identification sensor and an occlusion sensor. The membrane switch includes a first layer with a conductive pattern and a second layer with a conductive pattern. Each conductive pattern has an occlusion portion and an identification portion.

Figure 1A:
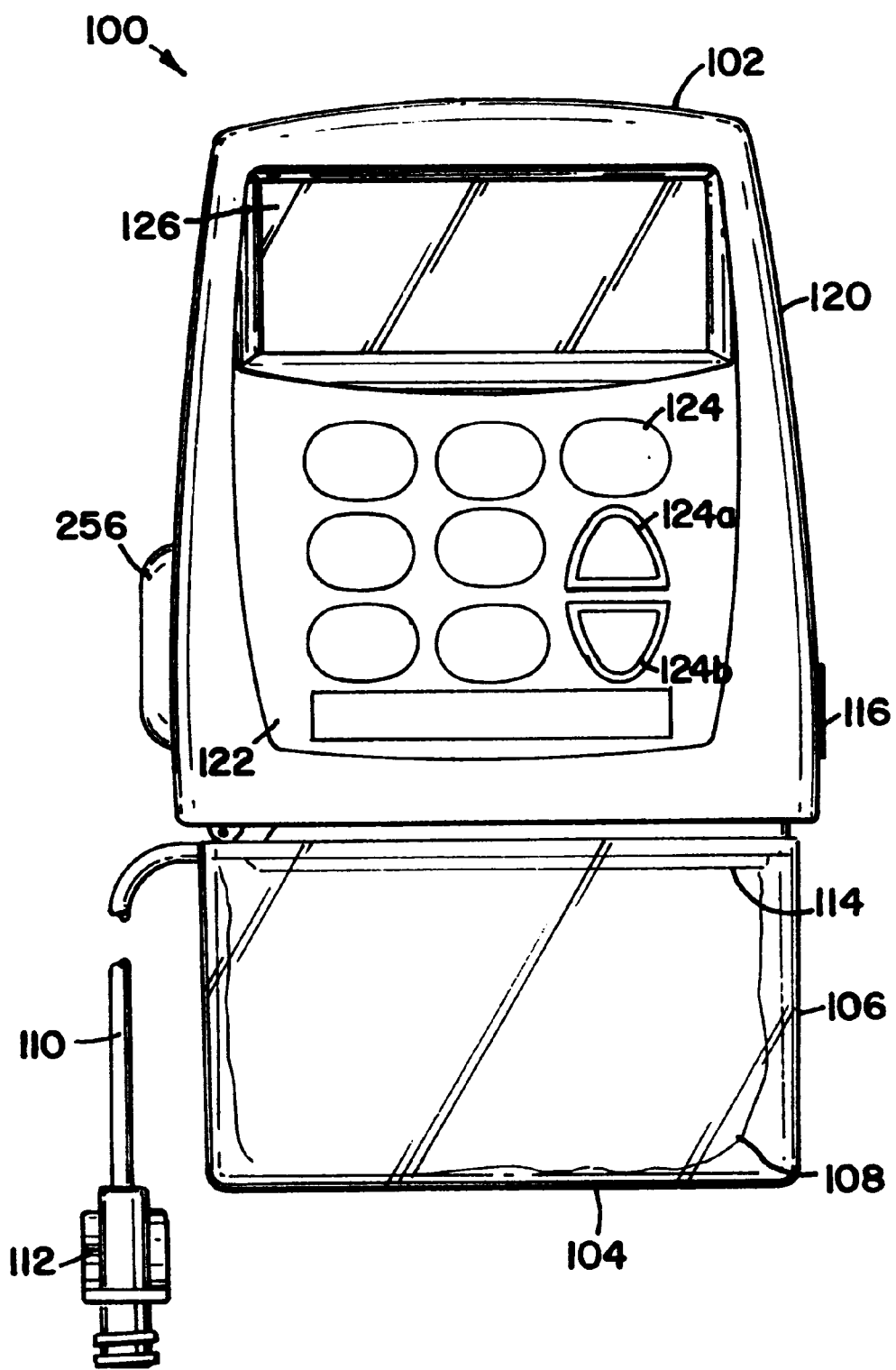
FIG. 1A is one embodiment of a drug pump including a control module and a drug cassette according to the present invention.
Figure 1B:
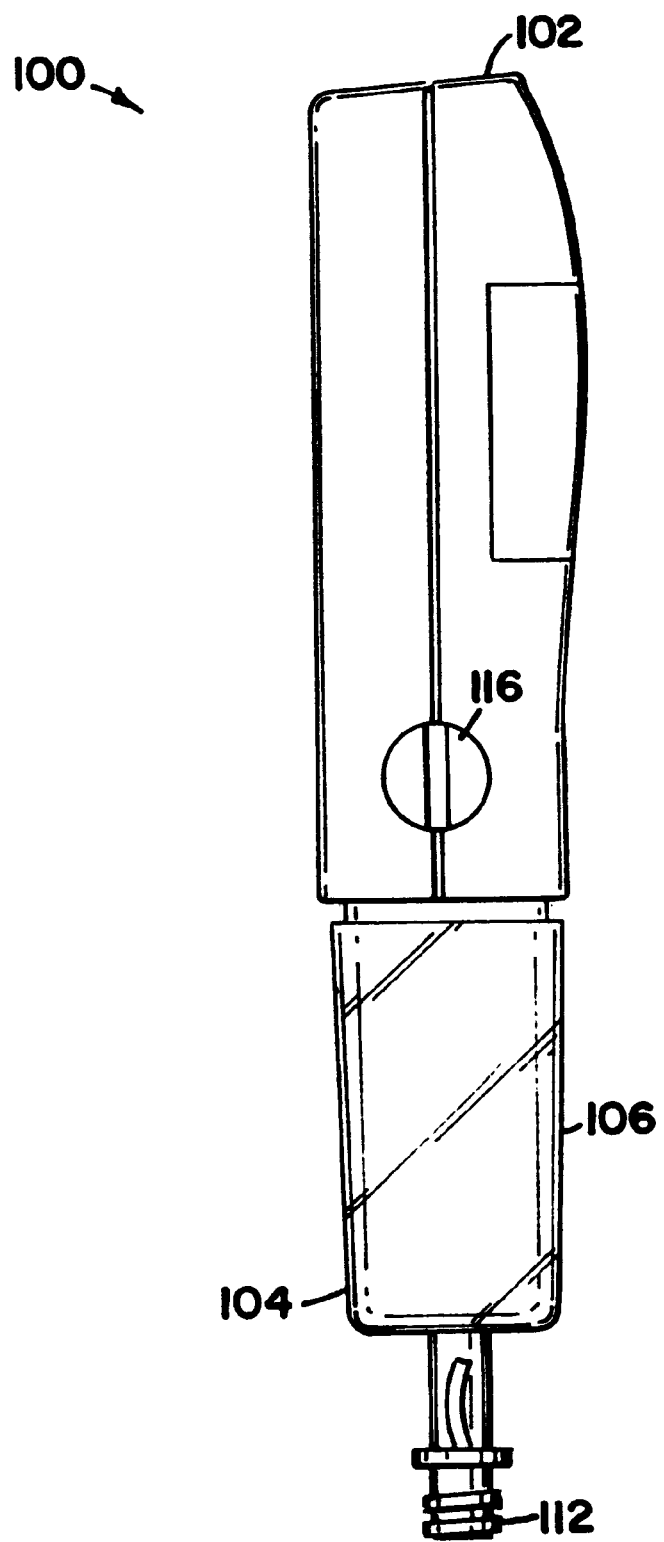
FIG. 1B is a right side view of the control module of FIG. 1 showing the latch for use in attaching the drug cassette to the control module.
Figure 1C:
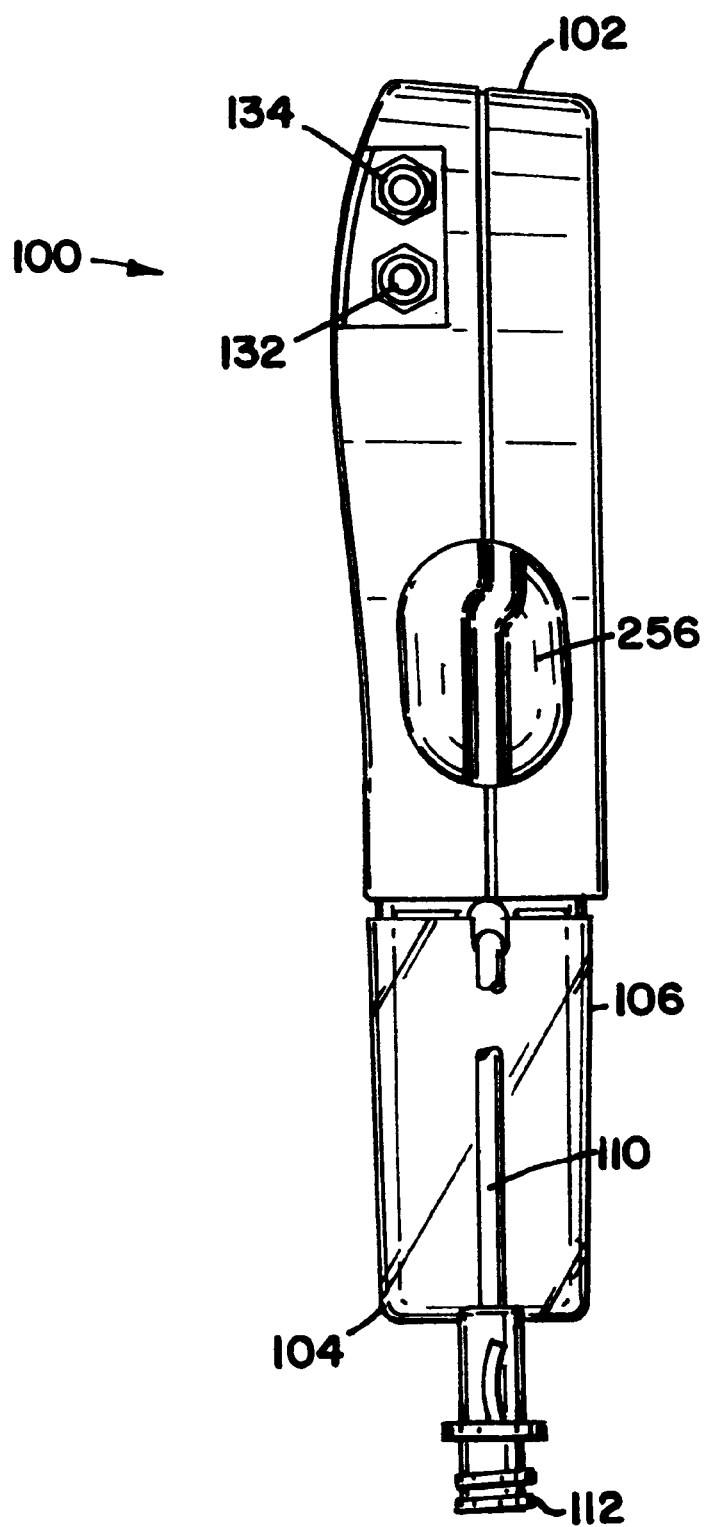
FIG. 1C is a left side view of the control module of FIG. 1 showing the external power port and the communications port.
Figure 5:
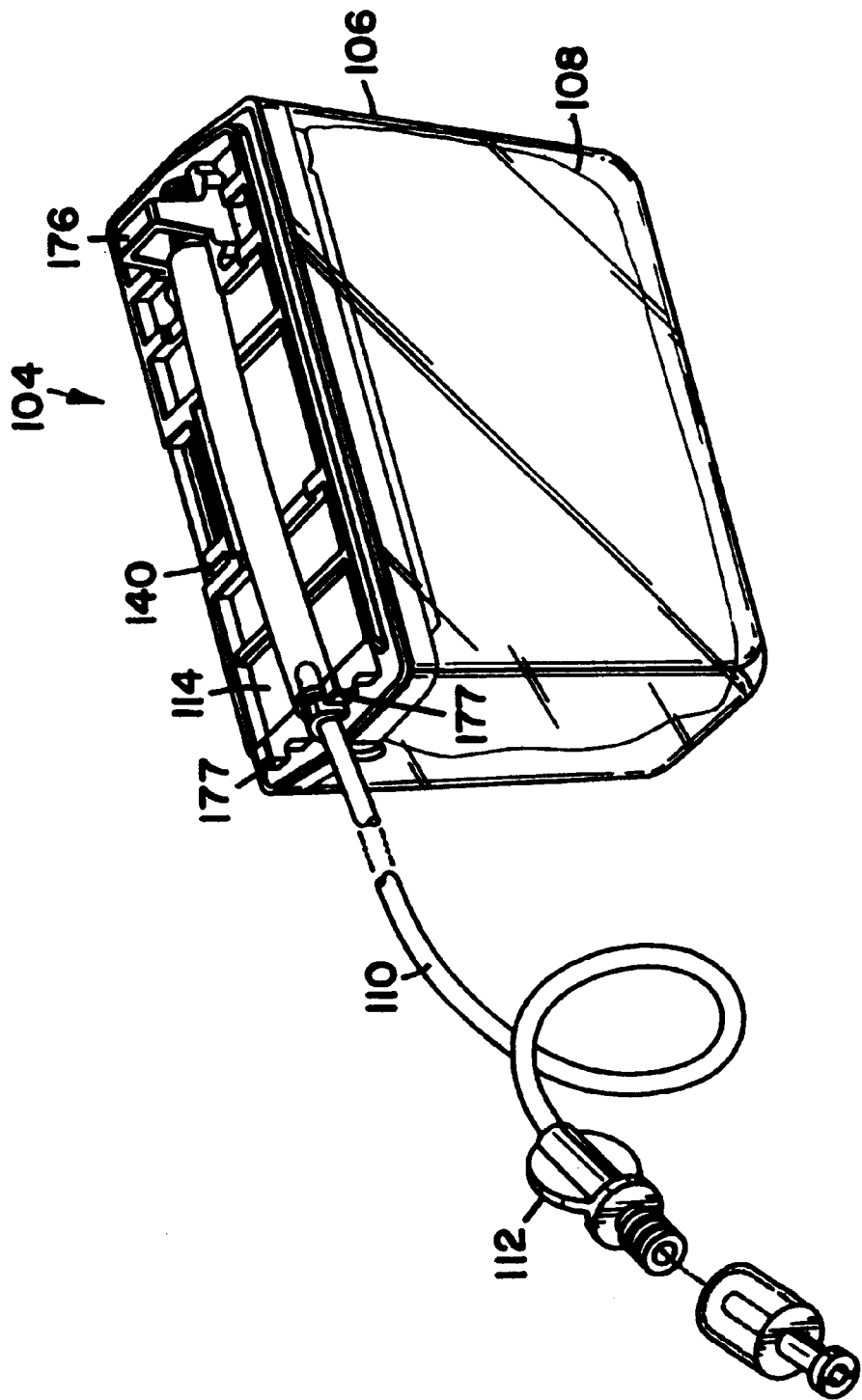
FIG. 5 is a front perspective view of a cassette having a projection for use with the drug pump of FIG. 1.

Referring now to FIGS. 1A–1C, a drug pump 100 includes a control module 102 which is selectively mounted to a cassette or cartridge 104. Cassette 104 is shown as including an outer housing 106 with a fluid reservoir 108 disposed within outer housing 106. Extending from fluid reservoir 108 and positioned adjacent control module 102 is a delivery conduit 110, or tubing, which is connectable to a patient, such as by a luer lock 112. Cassette 104 includes a pressure plate 114 which cooperates with a pump mechanism 141 (see FIG. 2) of control module 102 to pump fluid from fluid reservoir 108 through delivery conduit 110 to the patient. The cassette 104 and the pressure plate 114 that contacts the control module 102 is illustrated in FIG. 5.

Now referring to FIG. 4, an interface surface 178 is the portion of the control module 102 that contacts the cassette 104. The sensing device of the present invention 200 is positioned on the interface surface 178. The sensing device includes the occlusion sensor 206 and the identification sensor 208. The sensors 206 and 208 both operate by closing an electrical circuit when a membrane target area is depressed.

The occlusion sensor 206 is positioned on the interface surface 178 so that it will contact the delivery conduit 110 when the cassette 104 is attached to the control module. In FIG. 4, a downstream occlusion sensor 206 is pictured. An upstream occlusion sensor may also or alternatively be included in the sensing device 200, as will be discussed in greater detail in reference to FIG. 12. When the cassette is attached and the drug pump 100 is operating normally, the downstream occlusion sensor 206 is not depressed.

If the delivery conduit 110 becomes kinked or pinched at a location downstream from pumping mechanism 141, fluid flow will be stopped at the point of the pinch, preventing the fluid from reaching the patient. The pumping mechanism 141 includes an inlet valve 142, an expulsor 144, and an outlet valve 146. As the pumping mechanism 141 acts on the tubing 110 when a pinch occurs, pressure will build up in the tubing 110 between the kink and the pumping mechanism, causing the tubing 110 to expand. As the delivery conduit 110 expands, it will depress an occlusion target area 236 of the occlusion sensor 206, closing the electrical circuit of the occlusion sensing device 206. The occlusion sensor 206 is electrically connected to the control module 102.

The control module 102 performs a check for a closed circuit at the occlusion sensor 206 at predetermined intervals and alerts the patient if the circuit is closed, indicating an occlusion. The length of time between each check should be short enough to provide an alarm before the lack of medication would adversely affect the patient if a kink or pinch occurred.

In one embodiment, a check for the activation of the occlusion sensor 206 is performed after a pump cycle. At time intervals that are determined by the particular dose of drug to be administered, the pumping mechanism is activated, pressing a measured amount of the drug into the delivery conduit 110 for delivery to the patient. In between each pump activation, the drug pump processor may be programmed to be in a sleeping or reduced power state, to conserve power. The check for activation of the occlusion sensor 206 may take place at the end of each pump cycle, before the system partially shuts down, to conserve power. Preferably the occlusion sensor check takes place after the pump mechanism is activated, rather than during pumping, so that pressure increases in the delivery conduit during the pump stroke will not cause a false occlusion alarm. In many drug applications, the occlusion sensor will also be checked about once per second between each pump activation period.

The occlusion sensor 206 may be a digital sensor, and have either an on or off condition depending on whether there is pressure built up in the tubing 110 sufficient to depress the occlusion target area 236. As a result, a check for activation of the occlusion sensor may be performed using less power from the control module 102 than if the occlusion sensor reports a quantitative pressure reading.

Figure 13:
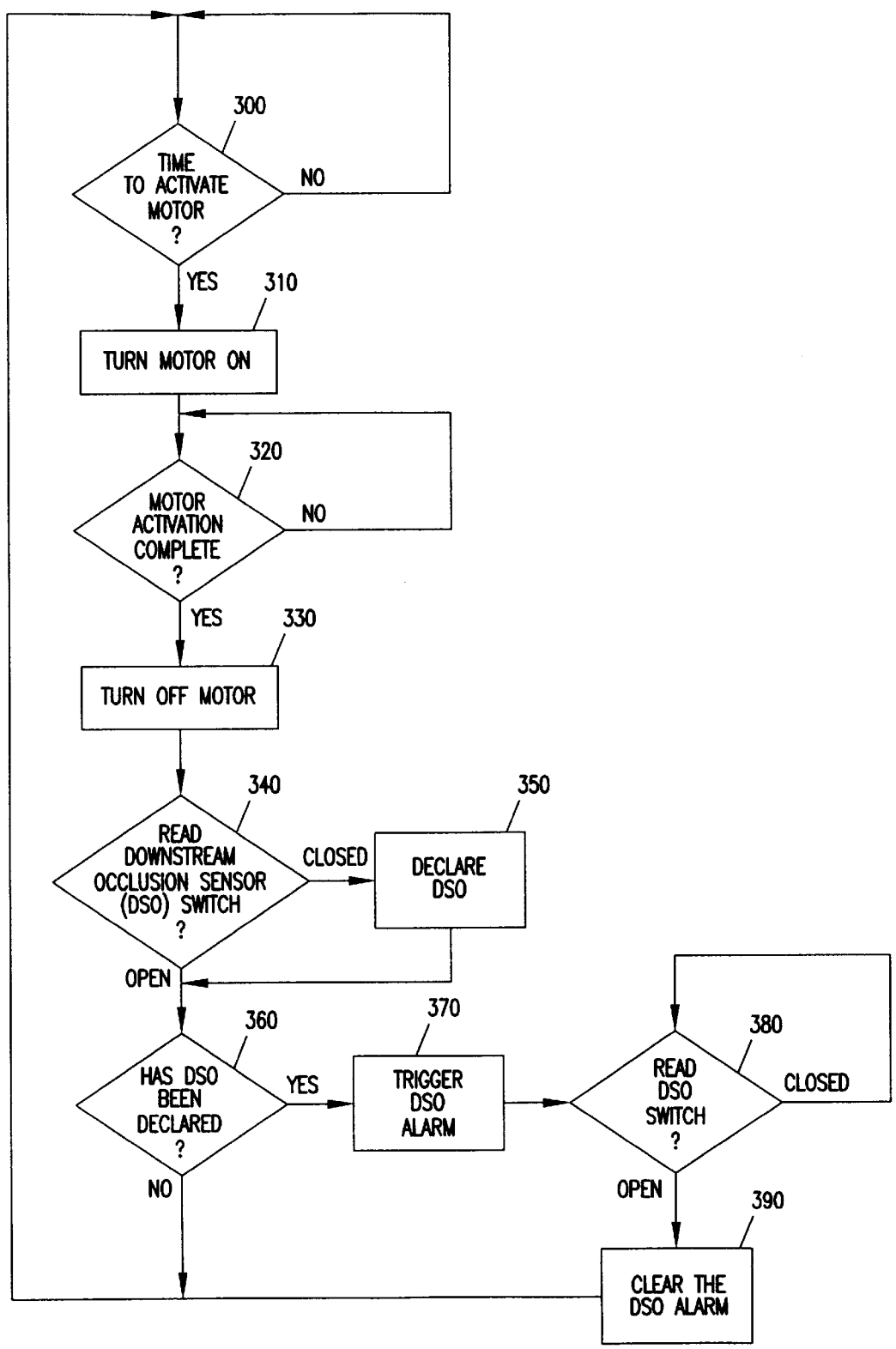
FIG. 13 is a flowchart of processing steps taken by the pump control module of the present invention.

The method for operating the downstream occlusion sensor of the present invention is described in FIG. 13. The control module 102 is in a sleep or rest state except when the pump is activated or when the sensors are read. To initiate the pumping cycle, the control module 102 first questions the system periodically as to whether it is time to activate the motor at step 300. If it is time to begin the pump cycle, the motor is turned on at step 310. The motor runs during the pumping cycle for a predetermined amount of time until the system determines that the motor activation cycle is complete at step 320, at which point the motor is turned off at step 330. Then the downstream occlusion sensor is read at step 340 to determine if the switch is open or closed. If the switch is closed, the system declares a downstream occlusion (DSO) at step 350. The next step determines whether a DSO has been declared at 360. If yes, an alarm is triggered at 370. The system then constantly checks to confirm that the DSO switch remains closed while the alarm is triggered at step 380. When the DSO switch is open, the alarm is cleared at step 390.

The occlusion sensor 260 described herein is located downstream from the pumping mechanism, namely the expulsor 144, inlet valve 142 and outlet valve 146. However, it is also possible that an occlusion could occur upstream of the pumping mechanism, namely between the inlet valve 142 and the fluid reservoir 108 or between the inlet valve 142 and the fluid reservoir 172 that is used with the adaptor 170. It may therefore be desirable to include an upstream occlusion sensor. Several types of upstream sensors are known in the art and some examples of such sensors are described in U.S. Pat. No. 5,695,473, which is incorporated herein by reference in its entirety.

Figure 12:
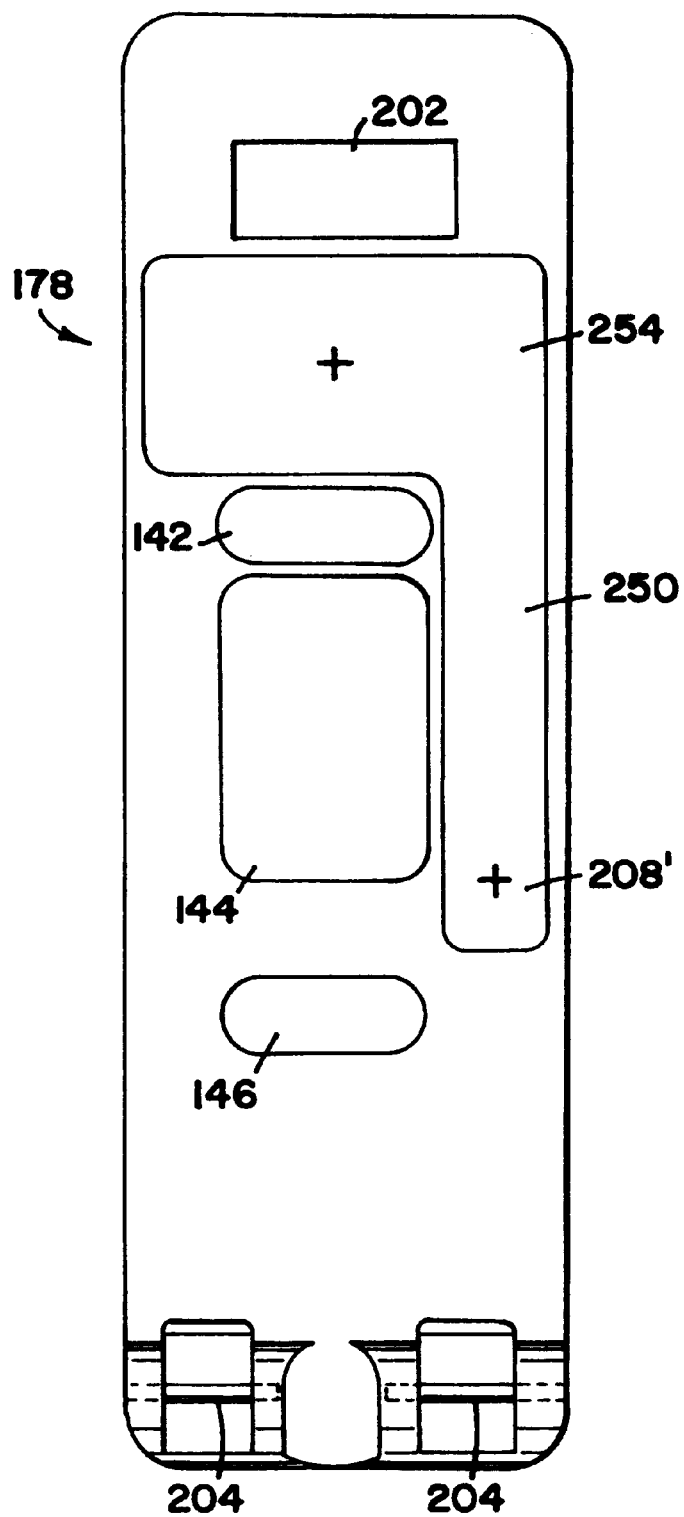
FIG. 12 is a bottom view of a chassis when the sensing device of the present invention is used as an upstream detector and cassette detector.

Now referring to FIG. 12, in an alternate embodiment of the present invention, a sensing device 250 could include an upstream occlusion sensor 254. When an upstream occlusion occurs, the pumping mechanism 141 acting on the tubing to move fluid may cause a low pressure condition to occur upstream of the pumping mechanism 141. One of many serious consequences of such a low pressure condition may be drawing the patient's blood back into the delivery conduit. An identification sensor 208' may also be included on alternate sensing device 250, similar in construction to identification sensor 208.

A low pressure condition caused by an upstream occlusion would cause the delivery conduit to decrease its cross-sectional area at a location upstream of the pumping mechanism 141. The change in shape of the delivery conduit could be accentuated by restricting the directions in which the conduit could contract, for example, by positioning reinforcing members on the sides of the conduit. The displacement of the conduit caused by low pressure would then result in a more dramatic decrease in the top profile of the delivery conduit at this location. According to the present invention, a membrane switch could be used to detect the under pressure condition cause by an upstream occlusion.

An upstream occlusion sensor 254 may include a first layer with a first occlusion conductive pattern and a second layer with a second occlusion conductive pattern. The conductive patterns, contact layer, spacer layer and other features of the upstream occlusion sensor 254 will be similar to the features described for the downstream occlusion sensor 206.

The upstream occlusion sensor 254 is configured to be in a closed position, with the two occlusion conductive layers in contact, during normal operation of the pump. The sensor 254 is held closed by the pressure of the contact between the delivery conduit and the occlusion sensor 254. When an upstream occlusion occurs, the delivery conduit at the upstream location will contract, reducing the pressure on the upstream occlusion sensor 254 so that the contact between the conductive patterns is broken, and an alarm sounds.

Figure 8:
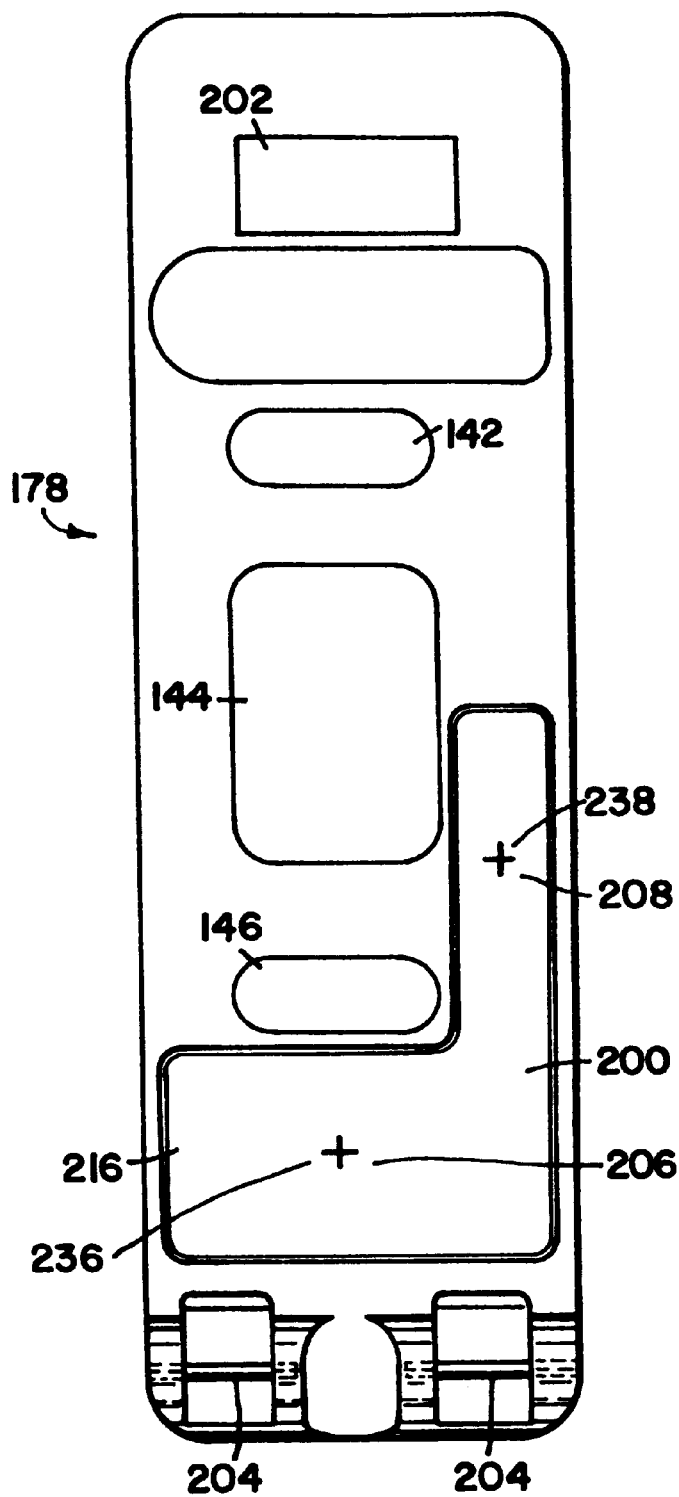
FIG. 8 is a bottom plan view of the control module of FIG. 1 after the sensing device of the present invention is included.

Now referring to FIG. 4 and FIG. 8, the identification sensor 208 is positioned on the interface surface 178 to be above a projection 140 on the cassette 104 (shown in FIG. 5), when the cassette is attached the control module 102. The identification sensor 208 is configured so that an identification target area 238 of the identification sensor 208 will be depressed by the cassette projection 140, during normal attachment, so that an electrical circuit within the identification sensor 208 is closed.

The identification sensor 208 is electrically connected to a processing unit in the control module 102. The control module 102 will perform a check before operating to ensure that the identification sensor 208 is activated. If the identification sensor 208 becomes deactivated during operation, the control module 102 will cease operation.

In one embodiment, the processing unit performs a check on the identification sensor 208 only at periodic intervals. A check is performed by applying an electric current to the identification sensor, and initiating an alarm mechanism if the circuit is not complete. If an electric current was constantly applied to the identification sensor, the identification conductive patterns may be heated, causing the identification conductive patterns to weld together. Preferably, the identification sensor is checked once during each pump activation period and about once per second between each pump activation period.

The identification projection 140 is useful to designate a cassette as being acceptable for use with a specific drug pump. The identification sensor 208 ensures that the drug pump 100 will only operate when designated cassettes, those having an identification projection 140, are attached. The identification sensor 208 also provides confirmation that the drug cassette 104 is actually attached to the control module.

The cassette 104 may have additional identification projections to indicate a specific type of cassette. For example, the pump surface 114 of the cassette 104 could have two additional projections, the presence or absence of which would indicate that a particular cassette was attached to the control module. The sensing device 200 would then have two additional projection sensors, and the control module could be programmed to accept only cassettes with a particular configuration or particular configurations of projections.

Figure 6:
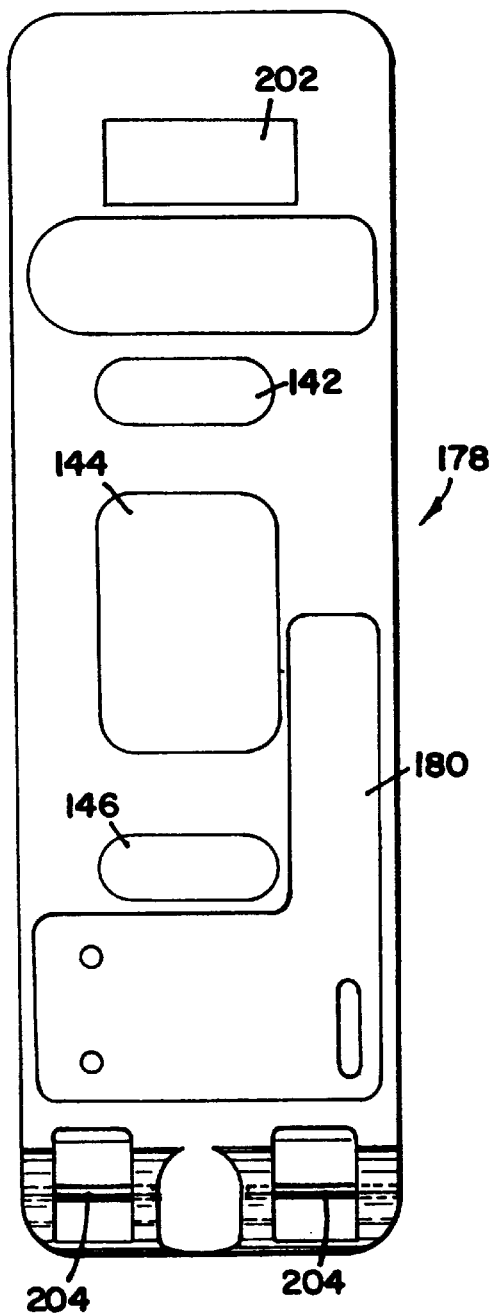
FIG. 6 is a bottom plan view of the control module of FIG. 1 before the sensing device of the present invention is included.

The construction of the sensing device 200 will now be discussed with relation to FIGS. 6–11, including the occlusion sensor 206 and the identification sensor 208. FIG. 6 shows the interface surface 178 of the control module 102 without the sensing device 200 attached. The sensing device 200 will be affixed to the area 180 on the interface surface. The sensing device 200 includes a first layer 218, a spacer layer 220, and a second layer 222, illustrated in FIGS. 9–11, respectively. A contact layer 216 may also be included as the exterior layer of the sensing device 200, as shown in FIG. 8. On the first layer 218, a first pair of conductive leads 240 connect the occlusion sensor 206 to an interface device that connects to the control module 102. A second pair of conductive leads 242 connect the identification sensor 208 to the interface device.

The outermost layer of the sensing device 200 is the contact layer 216 shown in FIG. 8 which is a bottom view of the control module 102 when the sensing device 200 is present. The contact layer 216 serves to protect the other layers of the sensing device 200 from contact with moisture, chemical or solvent penetration, extreme cold or heat, and wear and tear incurred in contacting the pressure plate 114 of the cassette 104. The contact layer 216 also provides the occlusion target area 236 and identification target area 238 where each sensor is activated. The target areas 236 and 238 of the contact layer 216 may be shaped to be concave toward the pump surface 114. When force is put on the occlusion or identification target areas 236 and 238 of the contact surface, the respective sensor is activated.

Figure 10:
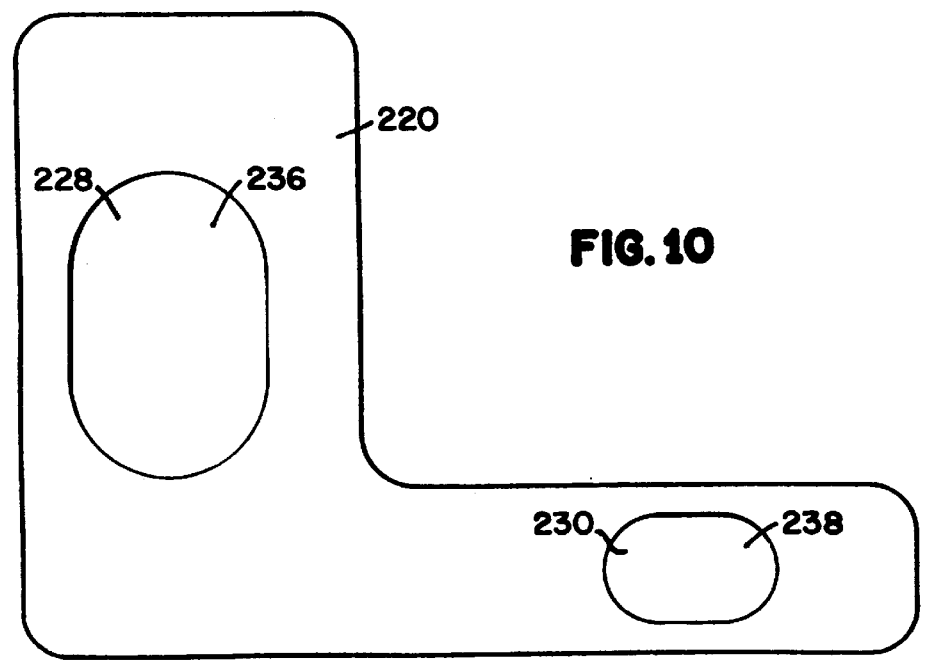
FIG. 10 is a top plan view of a spacer layer of the sensing device of the present invention.

The first and second layers include patterns of conductive material, which are described in detail herein. The spacer layer 220, shown in FIG. 10, provides a gap between the conductive patterns on the first and second layers. When force is placed against the sensor areas, the gap normally maintained by the spacer layer is eliminated and the two conductive patterns on the respective first and second layers come into contact with each other, closing a circuit. The gap between the conductive patterns could also be maintained without the use of a spacer layer, by shaping the second layer to be convex away from the first conductive patterns, so that a threshold force is required to bring the conductive patterns on the first and second layers in contact.

Figure 7:
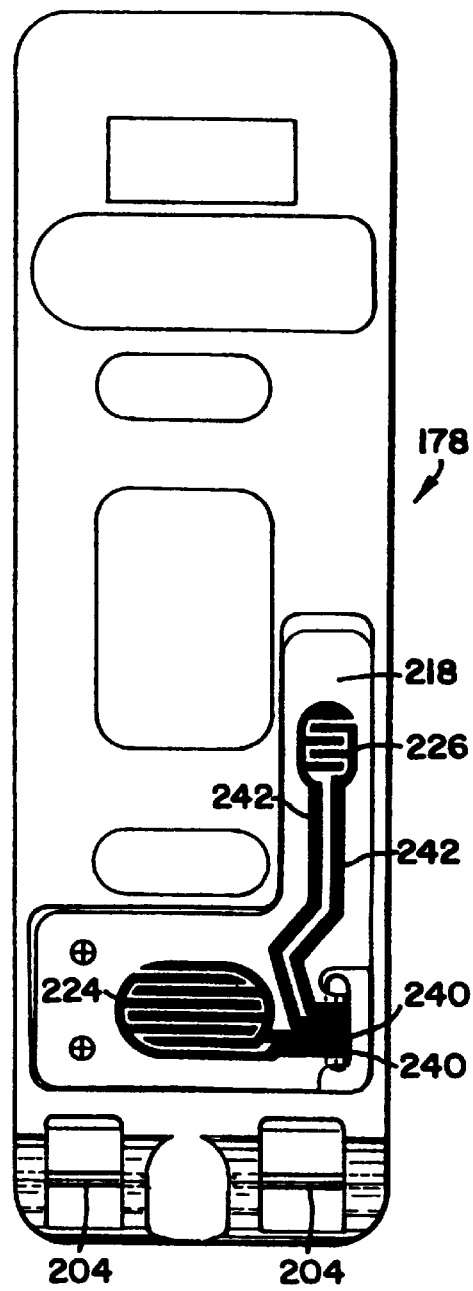
FIG. 7 is a bottom plan view of the control module of FIG. 1 where the first conductive pattern layer of the sensing device is present.
Figure 9:
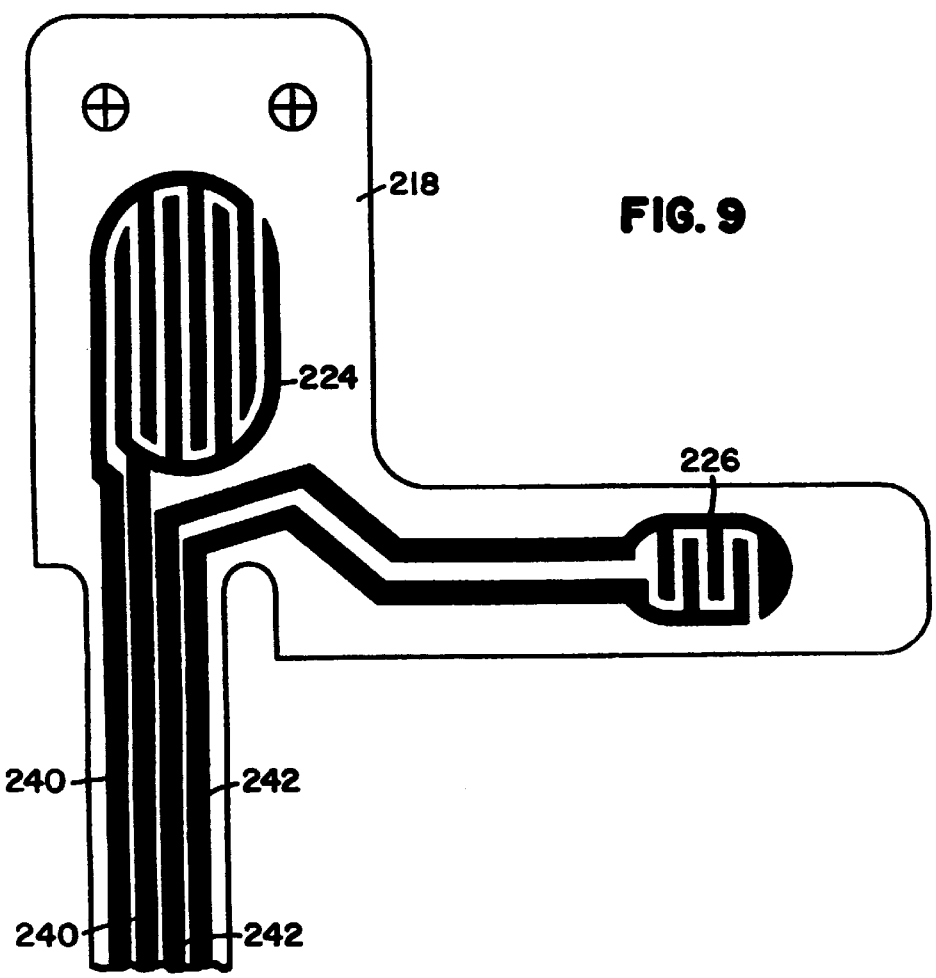
FIG. 9 is a top plan view of a first layer of the sensing device of the present invention.

The first layer 218 is shown in FIG. 7 positioned on the control module 102 and in FIG. 9 alone. The first layer 218 includes a first occlusion conductive pattern 224 and a first identification conductive pattern 226. The first occlusion conductive pattern 224 is part of the occlusion sensor 206. The first identification conductive pattern 226 is part of the identification sensor 208.

In one embodiment, the conductive patterns 224 and 226 on the first layer 218 consist of two sets of parallel lines of conductive material. Each set of parallel lines is connected to one of the conductive leads that communicate with the control module. The sets of parallel lines that make up of each conductive pattern 224 and 226 do not contact each other. The conductive pattern 224 and first pair of conductive leads 240, in combination with the circuitry in the control module 102 therefore make up an open electrical circuit. Likewise, conductive pattern 226 and the second pair of conductive leads 242 also make an open electrical circuit.

The optional spacer layer 220 is illustrated in FIG. 10. The spacer layer 220 includes an occlusion opening 228 and an identification opening 230, corresponding in shape and placement to the first occlusion pattern 224 and the first identification pattern 226 on the first layer.

Figure 11:
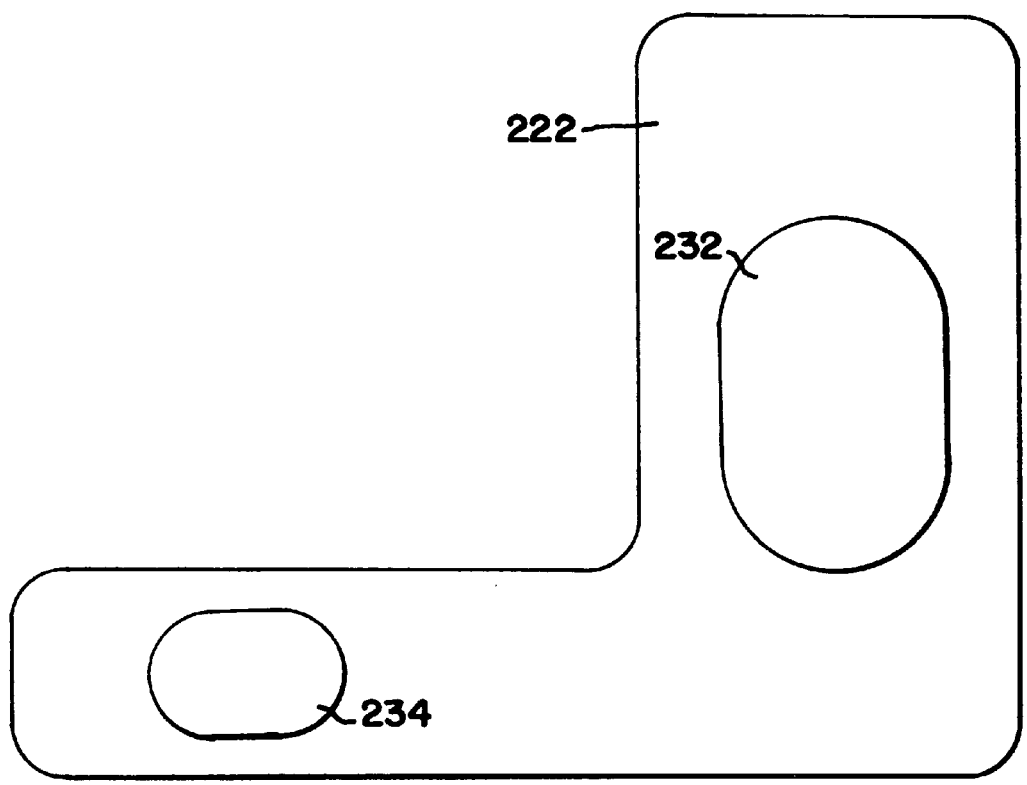
FIG. 11 is a top plan view of a second layer of the sensing device of the present invention.

The second layer 222 is illustrated in FIG. 11. The second layer includes a second occlusion conductive pattern 232 and a second identification conductive pattern 234. The second conductive patterns 232 and 234 are arranged so that contact with the first conductive patterns 224 and 226 will close the open circuits of the first layer 218. In one embodiment, the second conductive patterns 232 and 234 are areas of solid conductive material, as illustrated. In the alternative, the conductive patterns 232 and 234 of the second layer may be a set of lines or another pattern that could close the open electrical circuit of the first conductive patterns 224, 226 of the first layer.

The sensing device 200 may be assembled by adhering the spacer layer 220 to the first layer 218, aligned so that the occlusion opening 228 is aligned with the first occlusion conductive pattern 224, and the identification opening 230 of the spacer layer 220 is positioned to be aligned with the first identification conductive pattern 226.

Next, the second layer 222 is adhered to the spacer layer in a similar manner. The second layer 222 may be adhered to the spacer layer 220 so that the second occlusion and identification conductive patterns 232 and 234 on the second layer are facing and aligned with the first occlusion and identification conductive patterns 224 and 226 on the first layer, respectively. In the preferred assembled sensor device 200, there are two sets of conductive patterns, each separated by a small space, a thickness of the spacer layer. A contact surface 216 may now be adhered to the second layer 222. The contact layer 216 may have two convex areas, positioned over the occlusion sensor 206 and the identification sensor 208, or may be flat based on the interface specifications of the delivery conduit 110 and the cassette projection 140.

The assembled sensor device 200 may be adhered to the interface surface 178 of the control module 102, as shown in FIG. 8. The layers may be joined to the interface and to each other using many different techniques that are known in the art. For example, an adhesive compound could be used to bond the first layer to the interface surface and the layers to each other. The adhesive compound used would be placed so that it would not interfere with the conductive properties of the conductive patterns or conductive leads. The position of the first and second layers may be reversed, without changing the scope of the present invention.

Momentary contact membrane switches are reliable, inexpensive to manufacture, easily replaceable, and have flexibility to be designed to optimize the switch response. Positioning the occlusion sensor and the identification sensor on a membrane switch provides these advantages to the drug pump 100 of the present invention. Because the membrane switch may be adhered to an external surface of the pump control module, repair or replacement of the sensing device may be performed easily without interfering with other components of the control module. The sensing device may simply be removed from the interface surface once the interface device is disconnected.

In addition, the construction of the membrane switch is versatile, allowing the ability to fine tune the switch contact characteristics. The size and shape of the contact area, the spacer size, shape and thickness may all be varied to produce the desired sensor sensitivity, actuation force, and other characteristics. The conductive pattern density can also be modified to optimize the response required by the switches.

The first layer, second layer, and spacer layer of the sensing device 200 may include a variety of different materials that are well known in the art of membrane switches. Materials that can support a conductive pattern and are durable under sustained pressure are preferably used. Two such examples of a material that could be included in the contact layer 216 are polyester and polycarbonate. The sensing device 200 may include commercially available components such as membrane touch switches manufactured by Topflight Corporation, 935 Borom Road, York, Pa. 17404.

The attachment of the cassette 104 to the control module 102 will now be described in relation to FIGS. 1–4. In FIG. 1A, fluid reservoir 108 is configured as a flexible fluid bag or pouch. Other fluid containers are possible. In addition, fluid reservoir 108 is shown contained within cassette 104. A remote fluid reservoir separate from cassette is possible, as discussed in connection with FIG. 3.

In FIG. 1B, latch 116 of control module 102 is rotatably operated to securely latch cassette 104 to control module 102. A lock may also be provided to prevent latch 116 from being unlatched, such as by an unauthorized person. In some drug therapies, such as pain medication, a locking of cassette 104 to control module 102 is required.

Now referring to FIG. 1A, control module 102 includes an outer housing 120 containing within the control system and pump mechanism 141. Control module 102 includes a keyboard 122 with a plurality of keys 124 including up and down arrow keys 124a, 124b for scrolling. Tactile structures can be provided to assist a user in distinguishing the keys 124 by feel. Keyboard 122 permits entry of information to pump 100. Control module 120 further includes a display 126 for displaying information concerning operation of pump 100. A visual indicator (not shown) such as an amber or green LED indicator may be provided with control module 120 to indicate various conditions of pump 100 to the patient or caregiver. The condition of the identification sensor 208 and/or occlusion sensor 206, for example, may be indicated by the visual indicator, a visual message on the display, an audible alarm, or a combination of these indicators.

Pump 100 is an expulsor or peristaltic infusion pump which includes pump mechanism 141 as shown in FIG. 2. Pump mechanism 141 squeezes tubing 110 in a particular manner to achieve pumping of fluid from the reservoir to the patient. Pump mechanism 141 includes a reciprocally mounted inlet valve 142, a reciprocally mounted expulsor 144 downstream of inlet valve 142, and a reciprocally mounted outlet valve 146 downstream of expulsor 144. The end of inlet valve 142 is moved by pump mechanism 141 to alternately open and close tubing 110. The end of expulsor 144 is moved by pump mechanism 141 to compress tubing 110 to pump fluid and to allow expansion of tubing 110 following compression. The end of outlet valve 146 is moved to compress tubing 110 to alternately open and close tubing 110. A rotatable cam shaft 154 is rotated by motor 156 through gearing 158. The various components of pump mechanism 141 are supported by a chassis disposed within housing 120 of control module 102. Cam shaft 154 preferably includes three rotatable cams 162, 164, 166 configured as shown in FIG. 2.

Preferably, cam shaft 154 is constructed and arranged with double lobes (180° per activation cycle) for each cam 162, 164, 166 for optimized energy consumption, such as described in U.S. Pat. No. 5,364,242, issued Nov. 15, 1994, the disclosure of which is incorporated herein by reference. Preferably, pump mechanism 141 is made in accordance with the methods described in U.S. Pat. No. 5,364,242. Other pump mechanisms are anticipated including finger style pump mechanisms, roller pump mechanisms, and other fluid pumping arrangements. Examples of further expulsor style infusion pumps are shown in U.S. Pat. Nos. 4,559,038; 4,565,542; 4,650,469; and 5,181,910, the disclosures of which are incorporated herein by reference.

Referring now to FIG. 3, a remote reservoir adaptor 170 is shown which is mountable to the control module 102 in a similar manner as cassette 104. However, instead of including a self-contained fluid reservoir 108, adaptor 170 is separate from remote fluid reservoir 172. Tubing 174 links remote fluid reservoir 172 to adaptor 170.

Adapter 170 includes an upper surface 175 with an identification projection 210, two extending hooks 177 and a loop 176 which permit releasable mounting to control module 102. See for example U.S. Pat. No. 4,565,542 previously incorporated by reference. Adapter 170 and cassette 104 may be both referred to as "cassettes." Hooks 177 engage a suspended pin assembly 204 on control module 102 and loop 176 is engaged by latch 116 to mount the cassette to control module 102. Latch 116 in the latched state holds loop 176 so that the cassette cannot be pivoted away from control module 102 about an axis defined by hooks 177 and the suspended pin assembly 204.

The various embodiments described above are provided by way of illustration only and should not be construed to limit the invention. Those skilled in the art will readily recognize various modification and changes which may be made to the present invention without strictly following the exemplary embodiments and applications illustrated and described herein, and without departing from the true spirit and scope of the present invention which is set forth in the following claims.

What is claimed is:

1. A sensing device for a pump control module designed for use with a cassette having a pump surface with a projection, the sensing device being positioned on an interface surface of the pump control module for sensing an occlusion condition in a delivery conduit and for sensing the projection on the cassette, the sensing device comprising:
   a first layer having a bottom surface with a first occlusion conductive pattern and a first identification conductive pattern; and
   a second layer having a top surface with a second occlusion conductive pattern aligned with the first occlusion conductive pattern of the first layer and a second identification conductive pattern aligned with the first identification conductive pattern of the first layer.

2. The sensing device of claim 1, further comprising a spacer layer positioned between the first layer and second layer, the spacer layer defining an occlusion opening between the occlusion conductive patterns and an identification opening between the identification conductive patterns.

3. The sensing device of claim 1, wherein the occlusion target area and identification target area of the second layer are shaped to be concave from the first layer.

4. The sensing device of claim 1, further comprising a contact layer next to the second layer, the contact layer comprising an occlusion target area aligned with the occlusion conductive patterns and an identification target area, aligned with the identification conductive patterns.

5. The sensing device of claim 4, wherein the occlusion target area and identification target area of the contact layer are shaped to be concave from the first layer.

6. The sensing device of claim 1, wherein the first layer further comprises:
   an interface device; and
   a first pair of conductive leads connecting the first occlusion conductive pattern to the interface device, and
   a second pair of conductive leads connecting the first identification conductive pattern to the interface device.

7. The sensing device of claim 1, wherein portions of the first layer, spacer layer and second layer are bonded together with an adhesive.

8. The sensing device of claim 1, further comprising a layer of adhesive bonding the first layer to the interface surface of the pump control module.

9. A pump control module for administering a drug to a patient through a delivery conduit, the control module being designed for use with a cassette having a pump surface with a projection, the control module comprising:
   an interface surface; and
   a membrane switch positioned on the interface surface, the membrane switch comprising a first layer with a conductive pattern, and a second layer with a conductive pattern;
   wherein the membrane switch includes an occlusion sensor and an identification sensor, the identification sensor configured to detect the projection on the cassette and the occlusion sensor configured to detect an occlusion in the delivery conduit.

10. The pump control module of claim 9, wherein the first layer further comprises:
    an interface device; and
    a plurality of conductive leads connecting the conductive patterns on the first layer to the interface device.

11. The pump control module of claim 9, wherein the first layer and second layer are bonded together with an adhesive.

12. The pump control module of claim 9, the pump control module further comprising:
    a pump mechanism for pumping fluid;
    a processor electrically connected to the pump mechanism; and
    a flash memory electrically connected to the processor for storing pump application information for control and operation of the pump mechanism.

13. The pump control module of claim 12, the cassette further comprising a fluid reservoir connected to the delivery conduit for fluid communication, wherein the cassette is configured to be mounted to the pump mechanism so that a portion of the delivery conduit is positioned between the pump mechanism and the pump surface.

14. The pump control module of claim 9, further comprising a layer of adhesive bonding the membrane switch to the interface of the pump control module.

* * * * *